United States Patent [19]

Babish et al.

[11] Patent Number: 5,496,703

[45] Date of Patent: Mar. 5, 1996

[54] INDIRECT IMMUNOASSAY FOR DIOXINLIKE COMPOUNDS

[75] Inventors: John G. Babish, Brooktondale; Sakina El-Tom, Ithaca; Xinfang Ma, Ithaca; Goeffrey Wheelock, Ithaca, all of N.Y.

[73] Assignee: Cornell Research Foundation, Inc., Ithaca, N.Y.

[21] Appl. No.: 132,164

[22] Filed: Oct. 5, 1993

Related U.S. Application Data

[63] Continuation of Ser. No. 795,193, Nov. 19, 1991, abandoned, which is a continuation-in-part of Ser. No. 792,922, Nov. 15, 1991, abandoned.

[51] Int. Cl.$^6$ ............................................. C12Q 1/02
[52] U.S. Cl. ....................... 435/7.21; 435/7.2; 435/7.24; 435/29
[58] Field of Search ...................... 435/7.2, 7.21, 435/7.23, 7.24, 813, 815, 29; 424/9

[56] References Cited

U.S. PATENT DOCUMENTS

| | | | |
|---|---|---|---|
| 4,238,472 | 12/1980 | Albro et al. | 436/540 |
| 4,798,807 | 1/1989 | Vanderlaan et al. | 530/388.9 |
| 4,891,322 | 1/1990 | Blackburn et al. | 436/64 |
| 4,904,595 | 2/1990 | Gierthy | 435/240.2 |

OTHER PUBLICATIONS

R. E. Clement, "ultraface Dioxin and Dibenzofuran Analysis: 30 Years of Advances," *Analytical Chemistry*, vol. 63, No. 23 (1991).
*Analytical News* (Sep./Oct. 1992).
D. E. Tillitt et al., "Characterization of the H4IIe Rat Hepatoma Cell Bioassay as a Tool for Assessing Toxic Potency of Planar Halogenated Hydrocarbons in Environmental Samples," *Environ. Sci. Technol.*, vol. 25, No. 1, pp. 87–92 (1991).
M. Vanderlaan, et al., "Environmental Chemistry—Improvement and Application of an Immunoassay for Screening Environmental Samples for Dioxin Contamnation," *Environmental Toxicology and Chemistry*, vol. 7, pp. 859–870 (1988).
M. Vanderlaan, "ES&T Critical Review—Environmental Monitoring by Immunoassay," *Environ. Sci. Technol.*, vol. 22, No. 3, pp. 247–254 (1988).
M. M. Stantostefano, et al., "Effects of Ligand Structure on the In vitro Transformation of the Rat Cytosolic Aryl Hydrocarbon Receptor," *Archives of Biochemistry and Biophysics*, vol. 297, No. 1, pp. 73–79 (1992).
J. C. Willey, et al., "Acute effects of 12–O–tetradecanoylphorbol–13–acetate, teleocidin B, or 2,3,7,8–tetrachlorodibenzo–p–dioxin on Cultured Normal Human Bronchial Epithelial Cells," *Carcinogenesis*, vol. 5, No. 2, pp. 209–215 (1984).
S. Safe, "Polychlorinated Biphenyls (PCBs), Dibenzo–p–Dioxins (PCDDs), Dibenzofurans (PCDFs), and Related Compounds: Environmental and Mechanistic Considerations Which Support the Development of Toxic Equivalency Factors (TEFs)," *Toxicology*, vol. 21, pp. 51–58 (1990).
S. Safe, et al., "Development and Validation of In Vitro Induction Assays for Toxic Halogenated Aromatic Mixtures: A Review," *Toxicology and Industrial Health*, vol. 5, pp. 757–775 (1989).
S. Collins, et al., "Carcinogen–Binding Proteins—High–affinity Binding Sites for Benzo[a]pyrene in Mouse Liver Distinct from the Ah Receptor ," *Molecular Pharmacology*, 26:353–359 (1984).
K. Steinberg, et al., "Assessment of 2,3,7, 8–Tetrachlorodibenzo–p–dioxin Exposure Using a Modified D–Glucaric Acid Assay," *Journal of Toxicology and Environmental Health*, 16:743–752 (1985).
C. A. Bradfield, et al., "A Competitive Binding Assay for 2,3,7,8–Tetrachlorodibenzo–p–Dioxin and Related Ligands of the Ah Receptors," *Molecular Pharmacology*, 34:682–88 (1988).
T. Zacharewski, et al., "Application of the in vitro Aryl Hydrocarbon Hydroxylase Induction Assay for Determining '2,3,7,8–Tetrachlorodibenzo–p–Dioxin Equivalents': Pyrolyzed Brominated Flame Retardants," *Toxicology*, vol. 51, pp. 177–189 (1988).
Bombick et al (1) PNAS 85 pp. 4128–4132 (1988).
Clark et al Mol. Pharm. 39 pp. 495–501 (1991).
Waithe et al (1) Biochem. Pharm. 41 pp. 85–92 (1991).
Waithe et al (2) Biochem. Pharm. 35 pp. 2069–2072 (1986).
Nebert et al Int. J. Biochem 21 pp. 243–252 (1989).
Bombick et al (2) Life Sciences 41 pp. 429–436 (1987).
Freedman et al Cancer Research 39 4605–4611 (1979).
Rijksen et al Anal. Biochem. 182 pp. 98–102 (1989) "A Nonradioactive Dot–Blot Assay fur Protein Tyrosine Kinase Activity".
Kramer et al Biochem. Biophys Res Comm. 145 #1 (1987) pp. 25–33 "2,3,7,8–Tetrachlorodibenzo–p–dioxin (TCDD) Enhances Antibody Production and Protein Kinase Activity in Murine B Cells".
Ma et al Biochem. Biophys. Res. Comm. 189 #1 (1992) pp. 59–65 "Protein Tyrosine Phosphorylation as an Indicator of 2,3,7,8–Tetrachloro–p–dioxin Exposure In Vivo and In Vitro".

*Primary Examiner*—Toni R. Scheiner
*Assistant Examiner*—Lora M. Green
*Attorney, Agent, or Firm*—Nixon, Hargrave, Devans & Doyle

[57] ABSTRACT

This invention relates to the determination of in vivo exposure to dioxinlike compounds and the in vitro quantitation of dioxinlike compounds based on protein tyrosine phosphorylation as mediated by the Ah receptor. The extent of protein tyrosine phosphorylation is determined by monoclonal antibodies to protein tyrosine phosphate. The amount and nature of protein tyrosylphosphate is quantitatively related to the in vivo or in vitro concentration of dioxin to which animals or cells were exposed. This method permits detection of dioxinlike compounds at concentrations in the parts per trillion and parts per billion range.

2 Claims, 12 Drawing Sheets 2,3,7,8-TCDF 3,3',4,4'-TCAB 2,3,7,8-TCDD 3,3',4,4'-TCBP

INDIRECT IMMUNOASSAY FOR DIOXINLIKE COMPOUNDS

This application is a "continuation" of application Ser. No. 07/795,193 filed Nov. 19, 1991, abandoned, which is a Continutation-In-Part of application Ser. No. 792,922 filed on Nov. 15, 1991, under Express Mail No. GB301854443 US, now abandoned.

BACKGROUND OF THE INVENTION

INTRODUCTION

Over the last several decades, dioxins have become the subject of intense public and scientific scrutiny. This is the result of not only their great toxicity but also their assumed widespread presence in the environment. The toxicology of dioxins has been addressed principally through studies of their mechanism of biological action using animal models and cell cultures systems. In addition the potential threat that dioxins present to human health has been addressed in only a limited manner through epidemiologic studies of populations known to have been exposed to dioxins. The environmental issues have been addressed through the study of the production, release and fate of dioxins and related substances. Although dioxins have been extensively studied during the last twenty years, the exact mechanism of toxicity of dioxins in biological systems and the extent of environmental distribution are unknown. This is due in part to a lack of a simplified method of assessing the exposure of biological systems to dioxin and related compounds.

TCDD AND RELATED CHEMICALS IN THE ENVIRONMENT

The term dioxin, as commonly used by the news media, is a shorthand for 2,3,7,8-tetrachlorodibenzo-p-dioxin (TCDD). TCDD is only one member (congener) of the polychlorinated dibenzo-p-dioxin family, of which there are 75 possible congeners whose structures vary according to the number and location of the chlorine atoms. A source of confusion is that the term "dioxin" is used to indicate either TCDD specifically, or the PCDD (polychlorinated dibenzodioxin) family in general. Biologically, TCDD is the most potent PCDD; most other PCDDs are less active by a factor ranging from several thousands to millions. TCDD has been studied most extensively of all the PCDD congeners.

Several other aromatic hydrocarbons share biological properties with TCDD, particularly when substituted with chlorine in the lateral positions. The most important of these are the polychlorinated dibenzofurans (PCDFs) and certain members of the polychlorinated biphenyl family (PCBs). The large number of possible PCDD (75), PCDF (135) and PCB (20) congeners greatly complicates environmental analysis, and complex clean up procedures are required before such analyses can be undertaken. As used herein, "dioxinlike" includes all members of these families of compounds and other compounds that induces the same cellular effects. TCDD came to scientific and public attention in the early 1970s in connection with the use of 2,4,5-trichlorophenoxyacetic acid (2,4,5-T) derivatives as herbicides and defoliants, notably through forest spraying programs in the U.S and in Viet Nam.

TOXIC AND BIOLOGICAL EFFECTS OF TCDD

The molecular properties of TCDD (chemically unreactive, nonpolar, lipid-soluble) make it typical of compounds that would be bioconcentrated from aqueous solution and stored in fatty tissue. In rodents, TCDD has a whole-body half-life on the order of weeks, which is short in comparison with the 5.8 year half-life for TCDD reported for a single male human. The toxic and biological effects of TCDD and related toxic halogenated aromatic hydrocarbons depend on a number of factors, such as the dose of the toxin, the route of administration and the species, age, strain, and sex of the animals. An intriguing aspect of TCDD-induced toxicity is the large species-dependence in the susceptibility to this chemical. Among rodents the $LD_{50}$ (lethal dose for 50% of the test population) varies over at least a 2500-fold range, from the highly sensitive guinea pig to the comparatively resistant hamster. This large variation in TCDD sensitivity between the guinea pig and hamster is not simply the result of differences in the rate of in vivo metabolism of TCDD, since the whole body half-life for TCDD only differs by 3-fold between these two species. A striking feature of TCDD's acute toxicity is that it does not cause death immediately. Animals suffer anorexia, and waste away over several days to weeks. The mechanism of feed refusal is unknown, but apparently does not involve a direct effect of TCDD on the brain.

The susceptibility of humans to TCDD is not known. Exposed subjects have reported a wide variety of lesions and symptoms. It has been difficult to attribute human deaths to TCDD with certainty, although a recent retrospective study of workers exposed occupationally to TCDD suggests an increase in soft tissue sarcoma with a latency period of 20 years. More work will be needed to assess the extent to which TCDD represents an environmental health threat. It seems reasonable to conclude at this time that humans are probably less susceptible to the effects of TCDD than most laboratory rodents, and it is certainly not justifiable to present the human risk from dioxin exposure as if it were the same as in the most susceptible species, the guinea pig.

In addition to overt physical symptoms, PCDDs and PCDFs also cause biochemical effects in both mammals and mammalian cells in culture. One ot the most notable and characteristic responses is the induction of microsomal benzo[a]pyrene hydroxylase (aryl hydrocarbon hydroxylase (AHH) and several related cytochrome P-450-dependent mono-oxygenases. The induction of drug-metabolizing enzymes serves the biological role of converting the inducer into a more water-soluble form so that it may be excreted. In terms of the induction of AHH and delta-ALA (delta-aminolaevulinic acid) synthetase activities, TCDD is orders of magnitude more potent than other inducers, such as 3-methyl-cholanthrene (MC). TCDD is the most potent member of the PCDD/PCDF families. Structure-activity trends indicate that induction (and toxicity) is associated mainly with congeners substituted in all of the 2,3,7 and 8 positions: these effects diminish by the addition of chlorine in non-lateral positions or removal of chlorine from the lateral.

One hypothesis for the slow toxicity of TCDD is that the elevated levels of cytochrome P-450 induced by the toxicant increase the rate of oxidation of membrane fatty acids and hence disrupt the integrity of cell membranes.

MECHANISM OF ACTION

A comprehensive mechanism describing the mode of TCDD action in animals would have to account, on a molecular basis, for all events from the initial exposure to the chemical through the development of overt toxic symptoms. It must account not only for the toxic and biological effects on several organ systems (e.g., lymphoid, hepatic, reproductive, etc.), but also for interspecies effects, and for biochemical phenomena such as the alteration of the levels of drug-metabolizing enzymes.

A large body of evidence suggests that the biological and toxic responses associated with TCDD and similar compounds are not the result of direct insult of the toxin. No evidence has been presented to substantiate the TCDD-induced formation of covalent adducts with proteins or nucleic acids. However, many of the toxic effects of TCDD have been shown to be mediated through a specific protein known as the Ah (aryl hydrocarbon) receptor. The sequence of events associated with a receptor-mediated mechanism can be rationalized in simple terms to involve (a) entry of the toxicant into the cells, (b) binding of the toxicant to the Ah receptor, (c) binding of the receptor ligand complex to DNA recognition sites, (d) expression of specific genes and the translation of their protein products, and (e) mode of action of the expressed proteins. A large gap exists in our knowledge between the initial events (a–c), which are understood reasonably well at the molecular level, and the final expression of overt toxicity (d and e).

The epidermal growth factor (EGF)-like effects of TCDD have been attributed to its ability to affect membrane components. For example, TCDD up-regulates plasma membrane EGF receptor levels and increases the activity of protein kinase C which is thought to activate EGF receptor through phosphorylation. More recent studies have shown that TCDD not only activates protein kinase C in certain cell lines but also phospholipase C.

EARLY EVIDENCE FOR A RECEPTOR PROTEIN

Early studies of genetic polymorphism in mice showed that 3-methylcholanthrene was capable of inducing AHH activity in the responsive C57BL/6J inbred mouse strain but not in the nonresponsive DBA/2 inbred mouse strain. Cross-breeding studies demonstrated that the responsive phenotype segregated as a dominant trait and, similarly to other aromatic hydrocarbon-induced responses, was governed by a single autosomal gene. This locus, apparently controlling a variety of responses to aromatic hydrocarbons, was deduced to be regulatory in nature and perhaps to encode a protein that regulated response(s) to this family of compounds.

The ability of TCDD to induce AHH and delta-ALA synthetase led researchers to postulate the existence of an induction receptor which could act as the transmembrane signal ultimately triggering the elevation of enzyme activities. The synthesis of radiolabelled TCDD led to the identification of a C57BL/6 mouse liver protein which specifically bound TCDD and exhibited all of the properties of a receptor. The importance of the discovery of this receptor, known as the aryl hydrocarbon (Ah) receptor (or occasionally as the dioxin receptor), is in providing a link between the action of TCDD at the molecular level and observable phenomena such as overt toxicity or changes in enzyme levels. In fact, current opinion is that all known effects of TCDD are probably Ah-receptor mediated.

One of the many unresolved questions in dioxin toxicology asks why organisms should possess a receptor for TCDD at all. One suggestion is that the Ah receptor evolved to detoxify the products of combustion (fire) such as benzo [a]pyrene which, like TCDD, binds to the Ah receptor with high affinity and also triggers the production of several mixed function oxidases. This would imply that the binding of TCDD to the Ah receptor is coincidental with TCDD assuming the role of some other exogenous ligand such as benzo[a]pyrene. Alternatively, TCDD may substitute for an endogenous ligand with an important, as yet undefined, physiological role. The search for the identity and function of this elusive natural ligand is the topic of intense study at the present time.

SPECIES AND TISSUE SPECIFICITY

The Ah receptor protein has been identified in the tissues from several mammalian and non-mammalian species. The C57BL/6J mouse strain has been found to possess relatively high hepatic levels of the Ah receptor capable of binding TCDD (40–120 fmol/mg of protein), and is very susceptible to TCDD-induced toxicity. By contrast, early studies showed the DBA/2 strain to possess low hepatic levels of TCDD binding Ah receptor (less than 1 fmol of receptor/mg of cytosolic protein) and to be relatively resistant to TCDD toxicity.

The Ah receptor has also been identified in several human tissues. The Ah receptor from human tissue is much like the receptor from the DBA/2 mouse liver and requires molybdate as a stablizing factor. In much the same way that steroid hormone receptors show tissue specificity, the Ah receptor has been detected in hepatic and several non-hepatic tissues that are susceptible to TCDD. In rats, the Ah receptor was detected in thymus, lung, liver, kidney, brain, testis and skeletal muscle, but not in the pancreas, adrenal glands or ventral prostate.

LIGAND SPECIFICITY

Structure-activity relationship studies for the binding of PCDDs and structurally similar halogenated aromatic compounds to the Ah receptor have shown that the ligand binding site is hydrophobic, and preferentially accommodates planar non-polar ligands having molecular dimensions approximating a 1.0 nm×0.3 nm rectangle. TCDD conforms most closely to the dimensions of the presumed binding site; it binds most strongly, and is also biologically the most potent congener of the PCDD family. PCDDs and PCDFs substituted with chlorine in at least three of the four tetra positions (2,3,7 and 8) bind most strongly to the Ah receptor. Removal of groups from these positions or the addition of chlorine atoms at non-lateral sites diminish the binding affinities markedly. Other compounds that are structurally similar to TCDD such as 3-methylcholanthrene also bind the Ah receptor with high affinity.

LIGAND BINDING

The affinity of a ligand for a receptor can be discussed in terms of kinetics (the rate of binding) or in terms of equilibrium (the intrinsic strength of the association). The distinction between these kinds of affinity has been a source of confusion in the receptor literature, and it is now clear that many equilibrium constants ($K_d$) previously reported for ligand-receptor association may not have the significance originally attributed to them.

Optimal Ah receptor-ligand binding in vitro requires an environment that is highly reduced, buffered at physiological pH and protected against calcium-dependent proteases. In addition, the binding of TCDD to the Ah receptor appears to be dependent on ATP and the presence of thiol groups. It has been suggested that the requirement for ATP may reflect a cyclic phosphorylation dephosphorylation of the Ah receptor induced by bound TCDD.

The equilibrium dissociation constant ($K_d$) for the interaction of TCDD with almost all Ah receptors studied to date has been deduced to fall in the nM range. Weaker binding has been observed with the unresponsive DBA/2 mouse and with the human receptor. These measurements have been made using Scatchard analysis, which is valid only if binding is a simple equilibration, free from side reactions. Unfortunately, the Ah receptors from most species are subject to rapid thermal inactivation in vitro, which render them unable to bind ligand. Under these conditions the use of an equilibrium method such as Scatchard analysis to measure binding affinity will underestimate the true strength of binding. More recent studies indicate that binding is substantially stronger than previously supposed. Newer experimental approaches have led to the conclusion that the $K_d$ values are not nM but in the pM range.

The rate of TCDD binding in vitro to the hepatic Ah receptor from several rodent species has been studied. In all cases, binding is rapid (saturation half-life at room temperature is less than 1 hour for a ligand concentration of $10^{-9}M$) and is associated with a substantial enthalpy of activation which can be associated with a reorganization of hydrogen bonds at the transition state. The enthalpy term is counterbalanced by a large positive entropy of activation, which can be explained as a hydrophobic effect, i.e., with loss of solvation of the binding site by water and the conversion of water of solvation to bulk water. This interpretation is consistent with a substantial conformational change in the protein concurrent with binding. This is similar to studies with the estrogen receptor whose unoccupied and liganded forms have been deduced to differ conformationally.

Quantitative structure-activity relationships (QSAR) have been used to study the relative affinities of different PCDD, PCDF, and PCB congeners for the Ah receptor from a number of species including humans. The consistent finding is that affinity correlates strongly with the lipophilicity of the ligand, again emphasizing the hydrophobic nature of receptor-ligand binding. However, the importance of other parameters such as hydrogen bonding ability and electron-donating or -withdrawing ability of the substituents differs among chemical families. Based on the data that are presently available, toxicity appears to correlate strongly with the binding affinity of the ligand for the Ah receptor.

OBJECTS OF THE INVENTION

Various objects, advantages and features of the present invention will be readily apparent from the ensuing detailed description and the novel features will be particularly pointed out in the appended claims.

These and other objectives are met by the present invention.

SUMMARY OF THE INVENTION

This invention provides an immunoassay that utilizes properties of ligand-receptor interaction such as binding to ligands with high affinity and specificity, mediating signal transduction patterns within a cell, and ability to differentiate genetic isoforms of receptors, enzymes and cellular proteins that are involved with ligand-receptor interactions. Various ligands or materials associated with ligand-receptor interactions can be detected and quantitated indirectly by measuring ligand-receptor complexes or the results of the formation of ligand-receptor complexes.

In one embodiment of this invention, the indirect immunoassay of the invention quantitates several important classes of environmentally distributed chemicals including the dioxins, polychlorinated biphenyls and polycyclic aromatic hydrocarbons. An assay according to the invention does not detect the environmental contaminant directly with antibodies, but detects the interaction of an intercellular receptor and the contaminant of interest. The assay can be used in kits directly in the field and does not contain any environmental contaminants other than what may be present in the sample to be measured. The assay can be performed in minutes at lower costs than existing instrumental methods, and the results of several hundred air, water, or soil samplings can be reported on-site. The availability of on-site results allows for immediate evaluation of remediation efforts. This assay employs (i) simple extraction procedures with no clean-up steps to remove interfering substances, (ii) high sensitivity and (iii) high selectivity for the contaminant of interest.

A preferred embodiment of this invention relates to the in vivo and in vitro quantitation of dioxinlike compounds based on protein tyrosine phosphorylation (pTP) as mediated by the Ah (aryl hydrocarbon) receptor found in mammalian cells. The extent of protein tyrosine phosphorylation is determined by monoclonal antibodies to protein tyrosylphosphate. The amount and nature of protein tyrosylphosphate is quantitatively related to the in vivo or in vitro concentration of dioxin to which animals or cells were exposed. This embodiment permits detection of dioxinlike compounds at concentrations in the parts per billion and parts per trillion range.

This indirect immunoassay may be adapted to assess an individuals' previous chemical exposure to dioxins, polychlorinated biphenyls or polycyclic aromatic hydrocarbons. Examples of other assays that determine biological response as a measure of exposure to other environmental chemicals include serum cholinesterase activity as a reflection of exposure to organophosphate insecticides or levels of serum thiocyanate as a reflection of exposure to cigarette smoke.

In another embodiment of the invention, immunoassays that measure ligand-receptor interactions are used to phenotype tumor cells. Phenotyping a biopsy sample of a tumor would assist in the determination of appropriate therapeutic strategies for chemotherapy of neoplastic diseases. Particularly preferred embodiments would phenotype breast and colon cancer cells. The pTP phenotype of the Ah receptor may be determined for these tumor cells by treating a biopsy sample with a low concentration of TCDD. The appearance of an increase in pTP in the TCDD treated cells versus the untreated controls of the same tumor, would indicate potential therapeutic agents that would be most effective against the tumor.

Similarly, Ah pTP phenotyping of normal lymphocytes may be performed. An increase of pTP would indicate the presence of Ah receptor with high affinity for dioxinlike compound. The implication of this finding is that individuals with the high affinity phenotype would be more susceptible to the development of certain cancers following exposure to PCBs or polynuclear aromatic hydrocarbons.

Other features and advantages of the present invention will become apparent from the following description of the invention which refers to the accompanying drawings.

BRIEF DESCRIPTION OF THE DRAWINGS

The following detailed description, given by way of example, will best be understood in conjunction with the accompanying drawings, described as follows.

DETAILED DESCRIPTION OF CERTAIN PREFERRED EMBODIMENTS

EXAMPLE 1

Chemicals

Figure 1B:
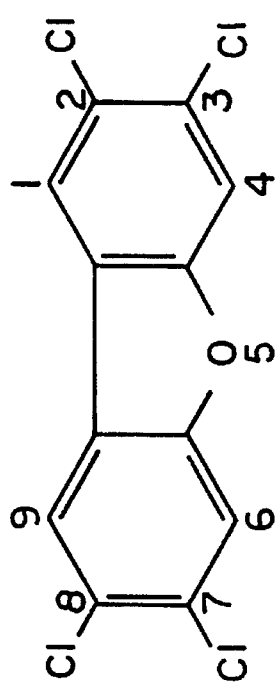
FIGS. 1(a)–1(d). Illustrates the chemical structure and associated ring numbering system for the tetrachloro congeners of PCDD and several other structurally related chemical families.
(a) TCDD=tetrachlorodibenzo-p-dioxin; (b) TCDF, tetrachlorodibenzofuran; (c) TCBP, tetrachlorobiphenyl; (d) TCAB, tetrachloroazobenzene.
Figure 1D:
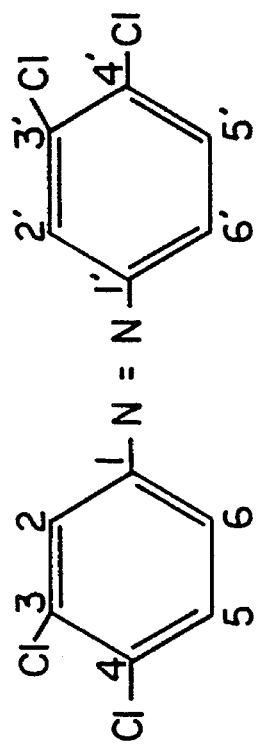
Figure 1A:
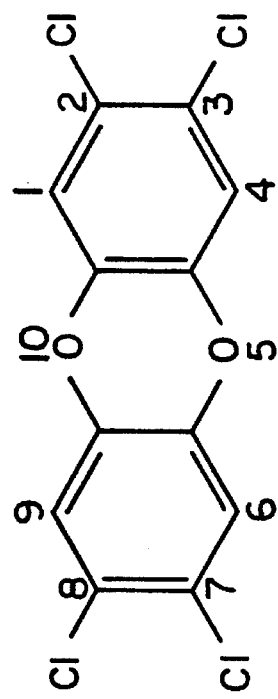
Figure 1C:
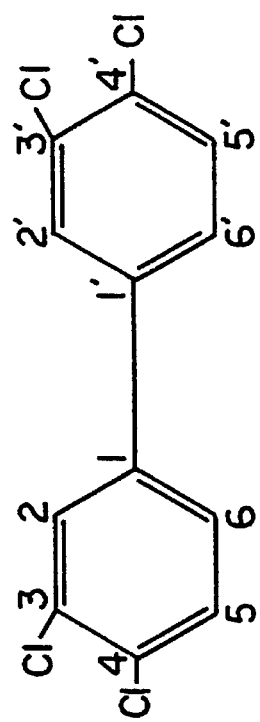

All chemicals were purchased from commercial sources and were of the highest purity available.

Animals

Female, C57BL/6 mice (or any cytochrome P-450IA1 inducible strain) were obtained from Harton Sprague Dawley (Indianapolis, Ind.). Experiments were performed using four to six week old, female mice weighing approximately 16 to 20 g. Mice were fed Prolab RMH 1000 rat, mouse and hamster food (Agway, Cortland, N.Y.) and received tap water ad libitum. All mice were housed three to five per cage and maintained on a photoperiod of 12 hours. Mice were killed 24 hours following an intraperitoneal injection of either corn oil alone or TCDD (Analabs) at 0.25, 0.5, 1, 2, 4, 10, 50 µg/kg, the volume of the injections ranged from 0.1 to 0.2 ml per mouse. Hepatic S-9 fractions were prepared by homogenizing the liver in 3 times the volume of 0.15M KCl. Following a 9000×g centrifugation for 20 minutes, the supernatant (S-9) fraction was carefully removed and quickly frozen for storage at −80° C.

ELISA

ELISA were performed with 96-well microtiter plates precoated with antigen. S-9 was used as antigen and was prepared as a series of geometric dilutions ranging from 0.4 to 500 μg protein/mL PBS. One-tenth mL from each dilution was promptly pipetted into the wells of a the microtiter plate in quadruplicate. Plates were incubated overnight at 4° C. After washing with 0.05% Tween 20 (polyoxyethylenesorbitan monolaurate) in phosphate buffered saline (PBS), individual wells were saturated with 0.2 mL bovine serum albumin (20 mg/mL in PBS) for 2 hours at 37° C. Wells were then incubated with antiphosphotyrosine monoclonal antibody (1.5 μg/mL ascites fluid) in 1 mg/mL bovine serum albumin and 0.05% Tween 20 in PBS, and bound for 1 to 1.5 hours at 22° C. Incubation with horseradish peroxidase-linked antimouse IgG (Sigma, St. Louis; 0.5×10³ mg IgG/mL PBS) and subsequent washing was performed as with the original monoclonal antibody. Peroxidase activity was determined after incubation with substrate (0.03% $H_2O_2$ and 1 mM 2,2'-azinodi(d-ethyl-benzthiazoline sulfonic acid-6) dissolved in 100 mM sodium citrate (pH 4.2) at 22° C. At the first visualization of color change $A_{415}$ values were recorded.

Immunoblots

The separation of S-9 proteins by means of SDS PAGE was performed by mixing the S-9 1:1 with a double strength sodium dodecyl sulfate sample buffer and heating the solution at 100° C. for 3 minutes prior to one-dimensional SDS polyacrylamide gel electrophoresis with 10% polyacrylamide. After electrophoresis, a Milliblot SDS electroblot apparatus (Millipore, Bedford, Mass.) was used to transfer the proteins from the polyacrylamide gels to an Immobilon™ membrane filter (Millipore). Complete transfers were accomplished in 25–30 minutes at 500 mA and were assessed by tracking pre-stained molecular weight standards onto the membrane filter. Membrane filters were blocked by incubating in TBS (Tris buffered saline) containing 5% milk for 30 minutes at 37° C. The membranes were then washed in TBST (TBS with 0.05% Tween 20) and incubated overnight with antiphosphotyrosine monoclonal antibody (1.5 μg/mL) in TBST. The primary antibody was removed, and the membranes were washed four times in TBST. To visualize the antibody reaction, the membranes were incubated for 3 hours at 37° C. with alkaline phosphatase-conjugated antimouse IgG diluted 1:1000 in TBST, washed 3 times in TBST, and developed for 15 to 30 minutes. Determination of molecular weights of immuno-stained proteins was performed by adding molecular weight standards (Bio Rad) to reference lanes and staining the membrane filters with amido black.

O-dealkylation Assay of Ethers of Resorufin

Resorufin (hydroxyphenoxazone) and ethoxyresorufin was purchased from Molecular Probes (Junction City, Oreg.). EROD was measured by following the increase in fluorescence due to the formation of resorufin by dealkylation of its ethoxy derivative. Reactions were carried out at 37° C. A baseline of fluorescence was recorded at an excitation wavelength of 530 nm and an emission wavelength of 585 nm. The reaction was started with the addition of NADPH and the dealkylation of the derivative to resorufin was followed by a progressive increase in fluorescence as resorufin was generated. Recordings were standardized by measuring the fluorescence of freshly generated resorufin from resorufin acetate (Sigma, St. Louis, Mo.) prior to each assay. The rates of metabolism are reported as pmole resorufin formed per minute per mg of S-9 protein.

Solutions—Stock of 1.0 mM resorufin acetate is made up in DMSO; place 50 μL aliquots in small tubes wrapped in foil; freeze at −20° C. until ready for use. Stock of 0.23 mM ethoxyresorufin is dissolved in DMSO; place 50 μL aliquots in small tubes wrapped in foil; freeze at −20° C. Stock of 50 mM phosphate buffer is made by adding 8.71 g $K_2HPO_4$ (MW 174.18) to 500 mL water along with 6.81 g of $KH_2PO_4$ (MW136.09). Stock of NADPH is made by dissolving 9.3 mg of NADPH (Sigma, St. Louis, Mo.) in 1 mL of water.

Protein Determination

Bicinchoninic acid was used for the spectrophotometric determination of protein concentration. Mix 100 μL of sample (standard or unknown) with 2 ml of working reagent in a test tube. Color development occurs by incubating at 37° C. for 30 minutes. Absorbance is read at 562 nm. Working reagent is made by adding 100 volumes of Reagent A with 2 volumes Reagent B. Reagent A: 1. g bicinchoninic acid (Pierce Chemical, Rockford, Ill.); 2 g $Na_2$—$CO_3$*$H_2O$; 0.16 g $Na_2$ tartrate; 0.4 g NaOH; 0.95 g $NaHCO_3$ make up to 100 mL with water, adjust pH to 11.25 with 50% NaOH. Reagent B: 4.9 g $CuSO_4$*$5H_2O$ to 100 ml in $ddH_2O$.

Densitometry

The indicated densitometric measurements were made on a BioImage AK Kodak Visage 110.

Results

Figure 2:
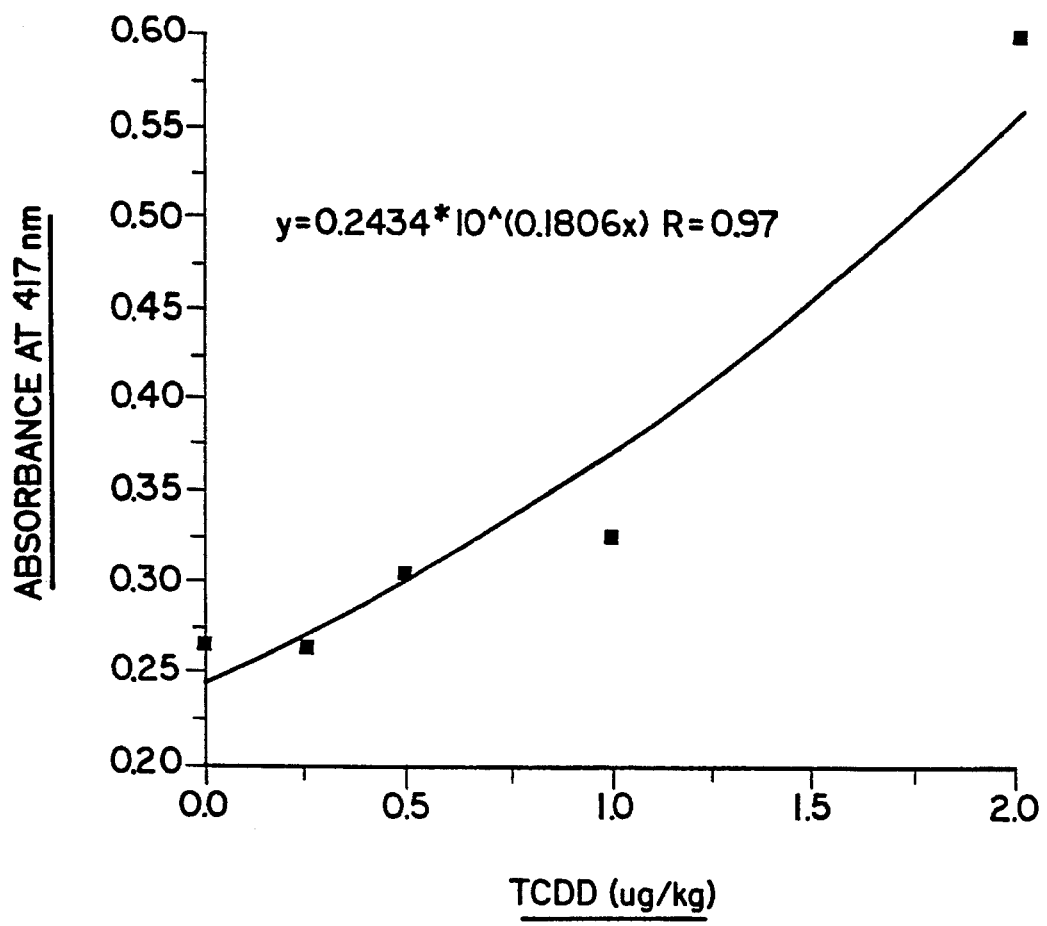
FIG. 2. Illustrates the dose-response relationship as determined by enzyme-linked immunosorbent assay (ELISA) for the example in which female C57BL/6 mice were given an intraperitoneal injection of various doses of 2,3,7,8-tetrachlorodibenzo-p-dioxin (TCDD) as described in Example 1, Section entitled: Animals. ELISA were performed with antiphosphotyrosine monoclonal antibody and the response measures total hepatic S-9 protein tyrosylphosphorylation 24 hours after dosing. Maximal total protein tyrosylphosphorylation was observed at 2 µg TCDD/kg and the median effective dose ($ED_{50}$) was 0.5 µg TCDD/kg.

Results of ELISA indicated a dose-response relationship in total hepatic S-9 protein tyrosylphophorylation (pTP) following the intraperitoneal administration of all doses of TCDD/kg. This overall hyperbolic increase was maximal at 2 μg TCDD/kg. FIG. 2 depicts the dose-response relationship for total hepatic S-9 pTP as a function of TCDD doses to 2 μg/kg. A log function of the form $y=0.2434*10^{(0.1806*x)}$ best described the increase in pTP over the 4 doses; the coefficient of determination was 0.97 for the relationship. The estimated dose for half-maximal pTP response ($ED_{50}$) was 0.5 μg TCDD/kg.

Figure 3:
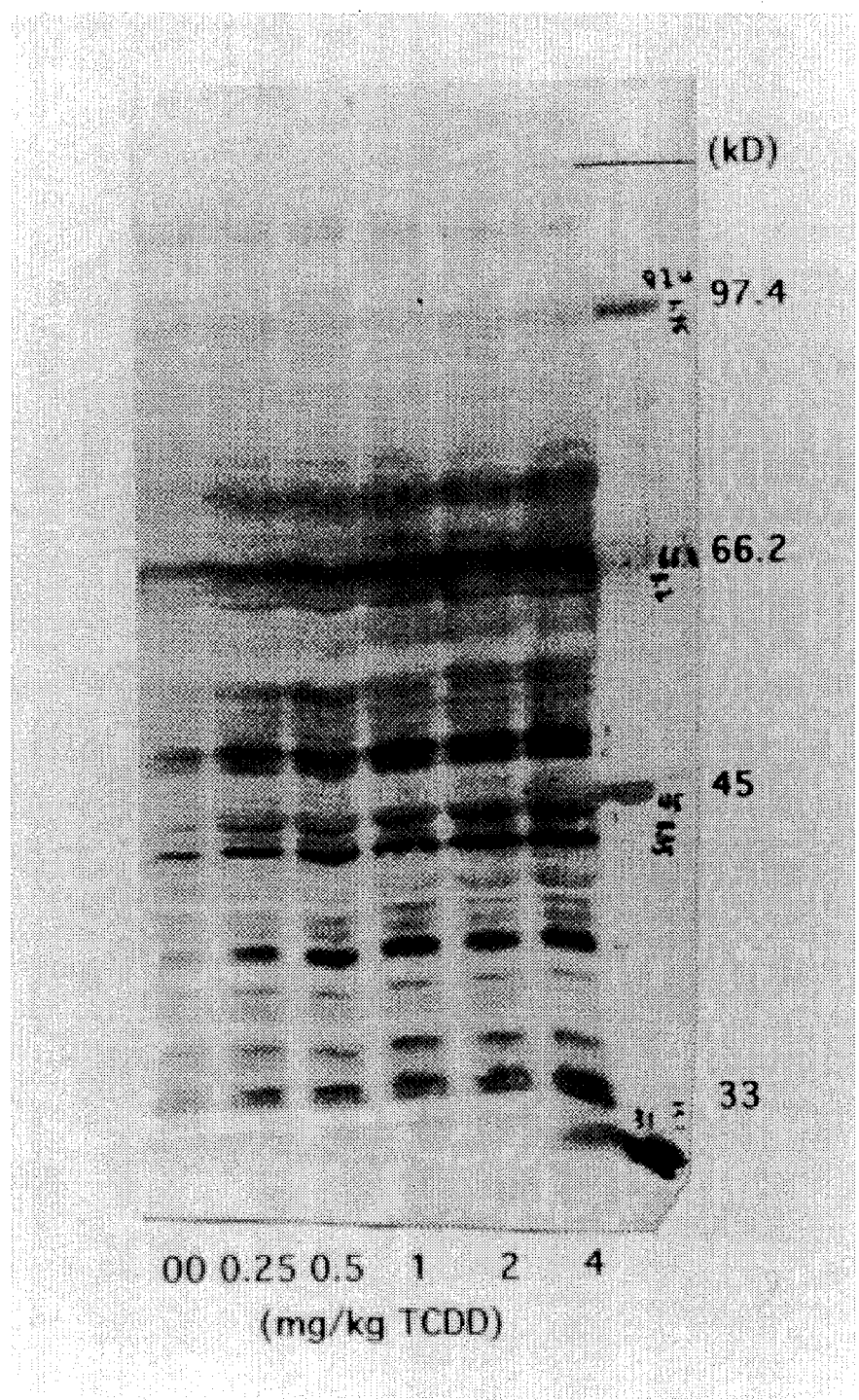
FIG. 3. Illustrates the immunoblot for total hepatic S-9 proteins and antiphosphotyrosine monoclonal antibody for the example in which female C57BL/6 mice were given an intraperitoneal injection of various doses of 2,3,7,8-tetrachlorodibenzo-p-dioxin as described in Example 1, Section entitled: Animals. TCDD dosing increased the pTP of 6 proteins in a dose-dependent manner. These proteins had approximate molecular weights of 37, 39, 44, 46, 51 and 52 kDaltons.

FIG. 3. Illustrates the immunoblot for total hepatic S-9 proteins with antiphosphotyrosine monoclonal antibody. TCDD dosing increased the pTP of 6 proteins in a dose-dependent manner for the 0.25, 0.5, 1, 2, and 4 μg TCDD/kg doses. These proteins had approximate molecular weights of 37, 39, 44, 46, 51 and 52 kDaltons. While 5 of these pTP were readily observable in the control lane, the 37 kDalton protein had only a faint band visualized in the control lane with the antiphosphotyrosine monoclonal antibody. This indicates that under normal conditions only extremely low levels of the tyrosylphosphorylated protein exist in the nontransformed hepatocyte, and the administration of TCDD resulted in the tyrosylphosphorylation of the 37 kDalton protein.

Figure 4:
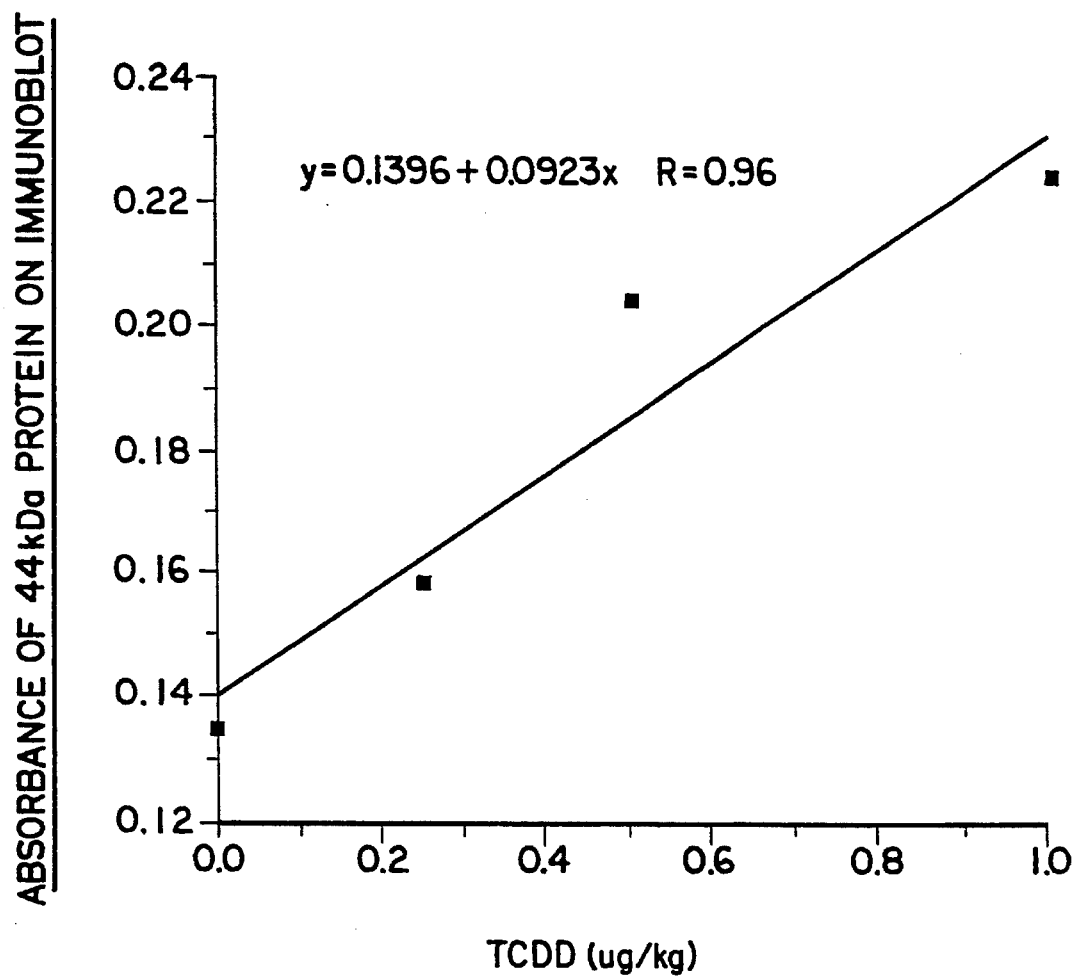
FIG. 4. Illustrates the dose-response relationship as determined by densitometer scanning of the 44 kDalton protein visualized by immunoblotting for the example in which female C57BL/6 mice were given an intraperitoneal injection of various doses of 2,3,7,8-tetrachlorodibenzo-p-dioxin (TCDD) as described in Example 1, Section entitled: Animals. Immunoblots were performed with antiphosphotyrosine monoclonal antibody and the response measures protein tyrosylphosphorylation of a 44 kDalton protein 24 hours after dosing. Maximal 44 kDalton protein tyrosylphosphorylation was observed at 1 µg TCDD/kg and the $ED_{50}$ was 0.05 µg TCDD/kg.

An illustration of the relationship between the tyrosylphosphorylation of the 44 kDalton protein and dose of TCDD to C57BL/6 female mice is presented in FIG. 4. Maximal tyrosylphosphorylation was observed at 1 μg TCDD/kg and the $ED_{50}$ for the tyrosylphosphorylation of this protein was 0.5 μg TCDD/kg. The relationship between dose of TCDD and the tyrosylphosphorylation of the 44 kDalton protein was linear to 1.0 μg TCDD/kg with a coefficient of determination of 0.96.

Figure 5:
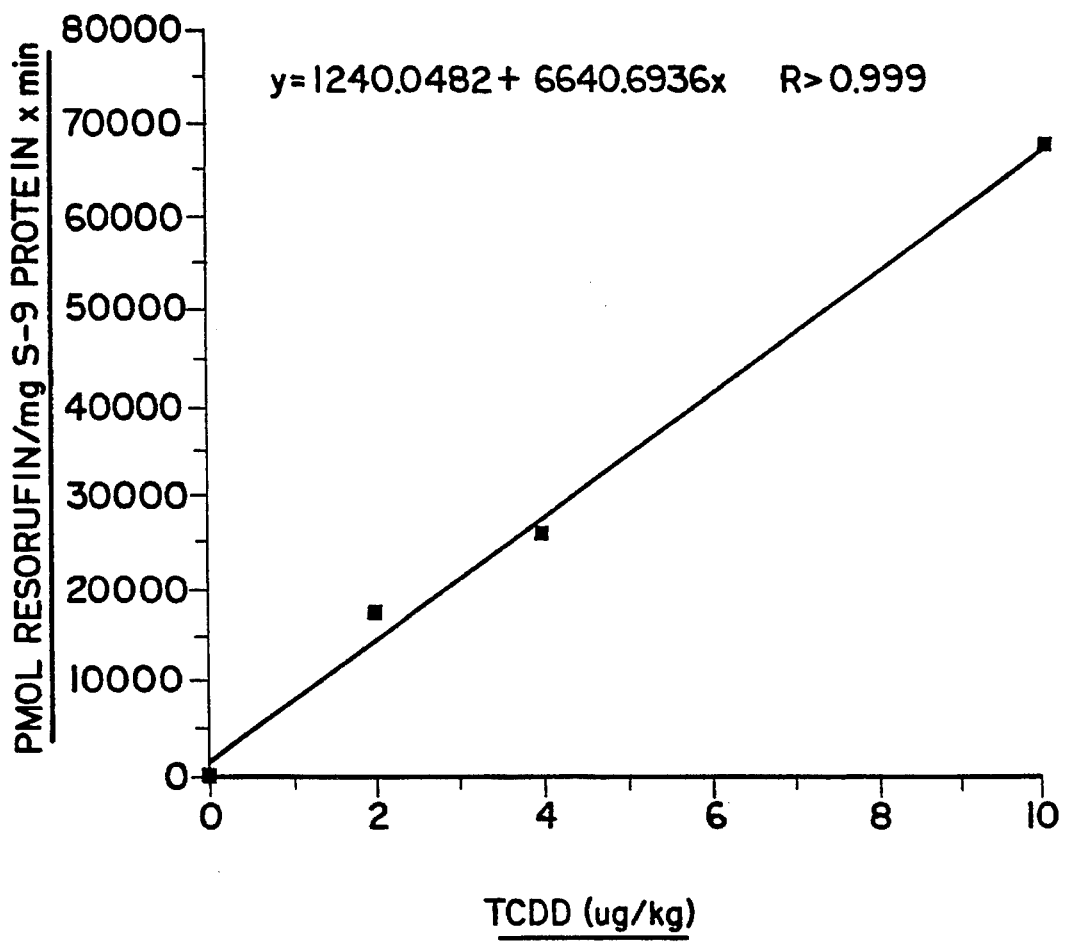
FIG. 5. Illustrates the dose-response relationship as determined by ethoxyresorufin O-deethylase assay (EROD) for the example in which female C57BL/6 mice were given an intraperitoneal injection of various doses of 2,3,7,8-tetrachlorodibenzo-p-dioxin (TCDD) as described in Example 1, Section entitled: Animals. EROD measures total hepatic S-9 cytochrome P-450IA1 as pmol of resorufin generated per mg protein-minute 24 hours after dosing. Maximal EROD activity was observed at 50 µg TCDD/kg and the $ED_{50}$ was 5 µg TCDD/kg.

Maximal induction of cytochrome P-450IA1, as determined by EROD activity, was observed at 50 μg TCDD/kg. The response was linear (R>0.999) to 10 μg/kg (FIG. 5) and became hyperbolic at the higher doses (not shown). The $ED_{50}$ for cytochrome P-450IA1 expression was 5 μg TCDD/kg. These results are in good agreement with published $ED_{50}$ values of approximately 3 μg/kg for the induction of cytochrome P-450IA1 aryl hydrocarbon hydroxylase specific activity 3 days post-injection (Poland, A. P., Glover, E., Robinson, J., Rand Nebert, D. W., J. Biol. Chem. 249, 5599, 1974).

This example illustrates several novel findings concerning exposure of normal animals to TCDD. First, exposure to TCDD results in an increase in intracellular protein tyrosine phosphorylation. At least 6 intracellular (S-9) proteins demonstrated an increase in tyrosine phosphorylation with increasing dose of TCDD. One of these proteins, a 37 kDalton protein existed constitutively in an extremely low state of tyrosylphosphorylation. In response to TCDD exposure, the 37 kDalton protein became highly phosphorylated at tyrosine residues. Second, the increased pTP observed with TCDD exposure is antecedent to the increase in cytochrome P-450IA1. Until now it was generally believed that the expression of cytochrome P-450IA1 was the most sensitive indicator of exposure to TCDD or dioxinlike compounds (Roberts, L., Science, 251, 624, 1991).

Although the increases in pTP were observed at much lower doses of TCDD than the induction of cytochrome P-450IA1, the dose-response curves of the two effects are parallel. Both effects were entirely described within 2 log units of dosing; the $ED_{50}$s for total protein or 44 kDalton pTP and EROD were clearly separated by a factor of 10. This parallelism of the 2 dose-response curves implies a common mediator. Since it is generally believed that all biological effects of TCDD are mediated through the Ah receptor (Roberts, L., Science, 251, 624, 1991), it is likely that the pTP response to TCDD is also mediated by the Ah receptor.

These results form the basis for a new hypothesis on the toxicity of TCDD. This hypothesis relates to the involvement of the Ah receptor in cell signal transduction activity. The interaction of a ligand with the Ah receptor is accompanied by a dephosphorylation of the Ah receptor and the activation of a phosphorylation cascade. The resulting phosphorylation cascade (principally tyrosyl phosphorylations) results in an alteration of normal homeostatic signaling. This altered signaling results in a pathognomonic condition for the cell and is the primary cellular lesion of dioxin and dioxinlike compounds.

EXAMPLE 2

Chemicals

All chemicals were purchased from commercial sources and were of the highest purity available.

Cell Cultures

The X3 human lymphoblastoma cells (Genetest, Wolburn, Mass.) were grown in 75 cm² T-flasks in RPMI 1640 medium (Gibco) containing 9% horse serum. Any cell or cell line expressing cytochrome P-450IA1 may be used. The cells were cultured at 37° C. in a 5% $CO_2$ (balance air) environment. Cells were subcultured by centrifuging (1000 rpm, 3 minutes) and resuspended in fresh media to a volume of 50 mL (at a cell density of $1.0 \times 10^6$ cells/mL). The TCDD-corn oil solution was homogenized with serum to a final concentration of 0.10 μg/mL. The TCDD-serum was added at concentrations of 0, 0.02, 0.05, 0.1, 0.5 and 1.0 nM per flask and incubated for 16 hours. After the appropriate incubation time, the cells were harvested by centrifugation and washed three times (PBS, 40° C.). A final cell count was then determined.

ELISA

ELISA were performed with 96-well microtiter plates precoated with antigen. X3 cell lysate was used as antigen and was prepared as a series of geometric dilutions ranging from 0.4 to 500 μg protein/mL PBS. One-tenth mL from each dilution was promptly pipetted into the wells of the microtiter plate in quadruplicate. Plates were incubated overnight at 4° C. After washing with 0.05% Tween 20 (polyoxyethylenesorbitan monolaurate) in PBS, individual wells were saturated with 0.2 mL bovine serum albumin (20 mg/mL in PBS) for 2 hours at 37° C. Wells were then incubated with antiphosphotyrosine monoclonal antibody (1.5 μg/mL ascites fluid) in 1 mg/mL bovine serum albumin and 0.05% Tween 20 in PBS, and bound for 1 to 1.5 h at 22° C. Incubation with horseradish peroxidase-linked antimouse IgG (Sigma, St. Louis; $0.5 \times 10^3$ mg IgG/mL PBS) and subsequent washing was performed as with the original monoclonal antibody. Peroxidase activity was determined after incubation with substrate (0.03% $H_2O_2$ and 1 mM 2,2'-azinodi(d-ethyl-benzthiazoline sulfonic acid-6) dissolved in 100 mM sodium citrate (pH 4.2) at 22° C. At the first visualization of color change $A_{415}$ values were recorded.

Immunoblots

The separation of cell lysate proteins by means of SDS PAGE was performed by mixing the cell lysate 1:1 with a double strength sodium dodecyl sulfate sample buffer and heating the solution at 100° C. for 3 minutes prior to one-dimensional SDS polyacrylamide gel electrophoresis with 10% polyacrylamide. After electrophoresis, a Milliblot SDE electroblot apparatus (Millipore, Bedford, Mass.) was used to transfer the proteins from the polyacrylamide gels to an Immobilon™ membrane filter (Millipore). Complete transfers were accomplished in 25–30 min at 500 mA and were assessed by tracking pre-stained molecular weight standards onto the membrane filter. Membrane filters were blocked by incubating in TBS (Tris buffered saline) containing 5% milk for 30 minutes at 37° C. The membranes were then washed in TBST (TBS with 0.05% Tween 20) and incubated overnight with antiphoshphotyrosine monoclonal antibody (1.5 μg/mL) in TBST. The primary antibody was removed, and the membranes were washed four times in TBST. To visualize the antibody reaction, the membranes were incubated for 3 hours at 37° C. with alkaline phosphatase-conjugated antimouse IgG diluted 1:1000 in TBST, washed 3 times in TBST, and developed for 15 to 30 minutes. Determination of molecular weights of immunostained proteins was performed by adding molecular weight standards (Bio Rad) to reference lanes and staining the membrane filters with amido black.

O-dealkylation Assay of Ethers of Resorufin

Resorufin (hydroxyphenoxazone) and ethoxyresorufin were purchased from Molecular Probes (Junction City, Oreg.). EROD was measured by following the increase in fluorescence due to the formation of resorufin by dealkylation of its ethoxy derivative. Reactions were carried out at 37° C. A baseline of fluorescence was recorded at an excitation wavelength of 530 nm and an emission wavelength of 585 nm. The reaction was started with the addition of NADPH and the dealkylation of the derivative to resorufin was followed by a progressive increase in fluorescence as resorufin was generated. Recordings were standardized by measuring the fluorescence of freshly generated resorufin from resorufin acetate (Sigma, St. Louis, Mo.) prior to each assay. The rates of metabolism are reported as pmole resorufin formed per minute per $10^9$ cells.

Solutions—Stock of 1.0 mM resorufin acetate was made up in dimethylsulfoxide (DMSO); μL 50 aliquots are placed in small tubes wrapped in foil and frozen at −20° C. until ready for use. Stock of 0.23 mM ethoxyresorufin was prepared in DMSO; placed μL 50 aliquots in small tubes wrapped in foil and frozen at −20° C. Stock of 50 mM phosphate buffer was made by adding 8.71 g $K_2HPO_4$(MW174.18) to 500 Ml water along with 6.81 g of $KH_2PO_4$(MW136.09). Stock of NADPH was made by dissolving 9.3 mg of NADPH (Sigma, St. Louis, Mo.) in 1 mL of water.

Results

Figure 6:
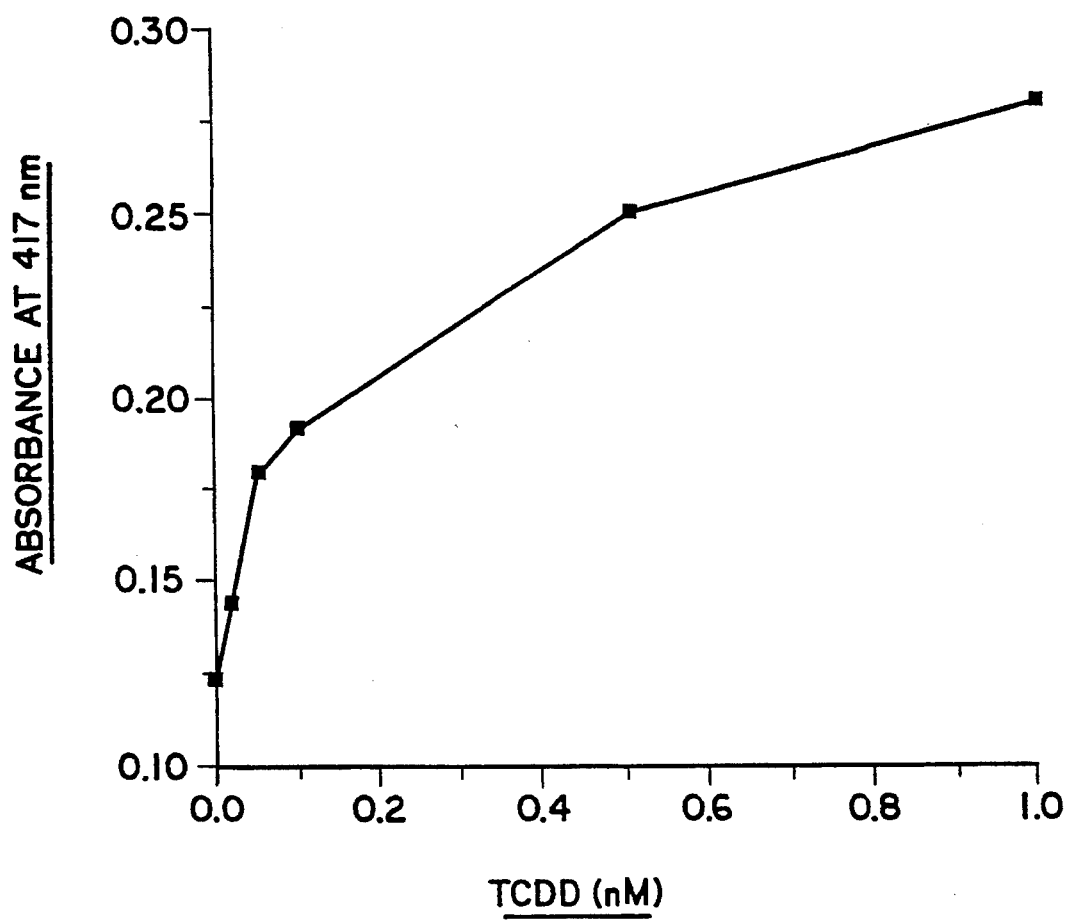
FIG. 6. Illustrates the dose-response relationship as determined by enzyme-linked immunosorbent assay (ELISA) for the example in which X3 human lymphoblastoma cells were exposed to various concentrations of 2,3,7,8-tetrachlorodibenzo-p-dioxin as described in Example 2, Section entitled: Cell cultures. ELISA were performed with antiphosphotyrosine monoclonal antibody and the response measures total cell lysate protein tyrosylphosphorylation 16 hours after dosing. Maximal total protein tyrosylphosphorylation was observed at 1 nM TCDD and the median effective concentration ($EC_{50}$) was 0.13 nM TCDD.

The dose-response relationship as determined by ELISA for the X3 human lymphoblastoma cells exposed to 0.02, 0.05, 0.1, 0.5 and 1.0 nM concentrations of TCDD is illustrated in FIG. 6. ELISA were performed with antiphosphotyrosine monoclonal antibody and the response measures total cell lysate protein tyrosylphosphorylation 16 hours after dosing. Maximal total protein tyrosylphosphorylation was observed at 1 nM TCDD and the $EC_{50}$ was 0.13 nM TCDD.

Figure 7:
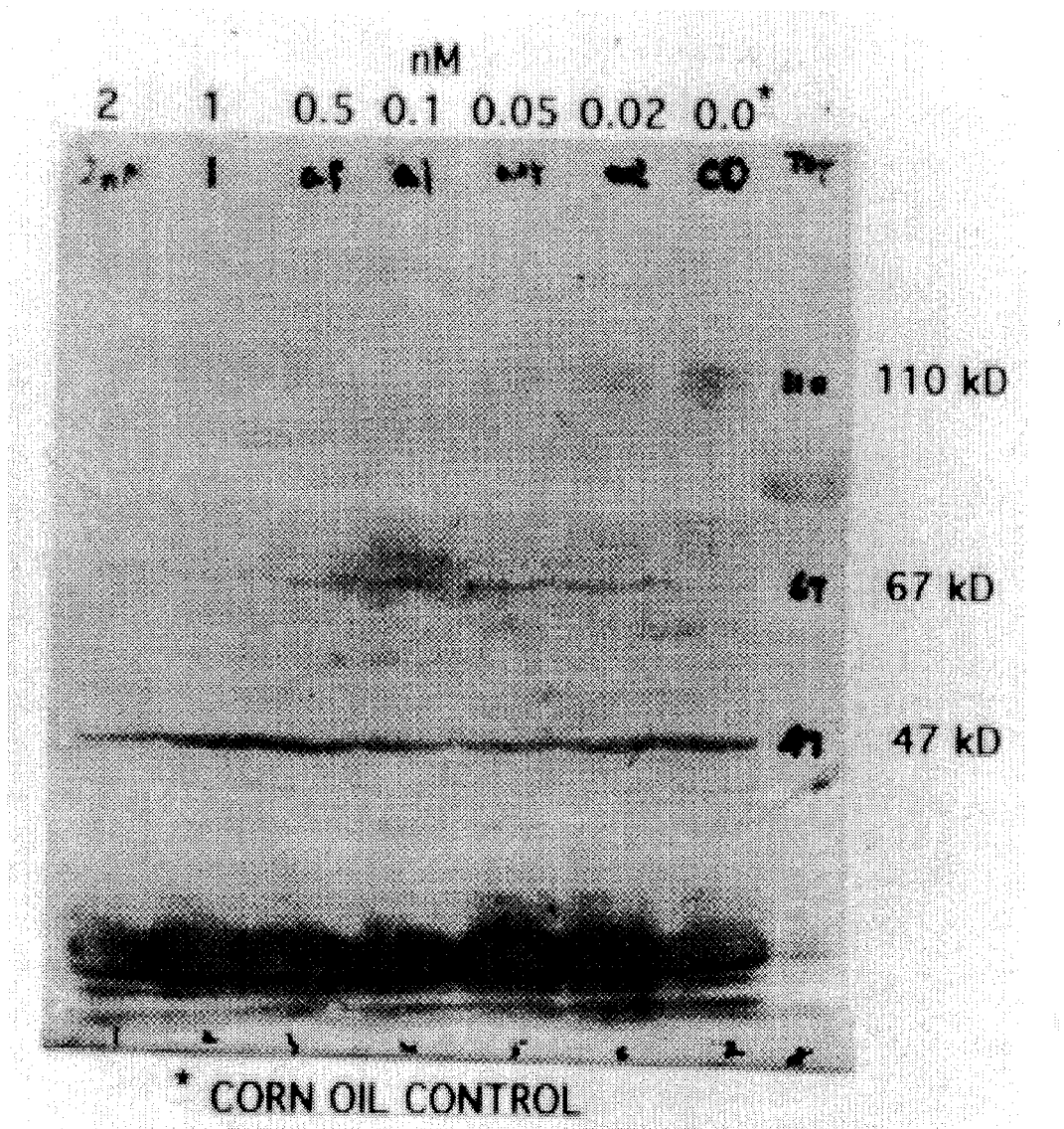
FIG. 7. Illustrates the immunoblot for total cell lysate proteins and antiphosphotyrosine monoclonal antibody for the example in which X3 human lymphoblastoma cells were exposed to various concentrations of 2,3,7,8-tetrachlorodibenzo-p-dioxin as described in Example 2, Section entitled: Cell cultures. The immunoblot depicts protein tyrosylphosphorylation 16 hours after exposure.

The immunoblot for total X3 human lymphoblastoma cell lysate proteins and antiphosphotyrosine monoclonal antibody indicates a dose response increase in pTP for 6 proteins (FIG. 7). The approximate molecular weights of these proteins were 47, 43, 42, 35, 33 and 28 kDaltons. A single pTP at 57 kDaltons was not apparent in untreated X3 cell lysate, but appeared in all X3 cells treated with TCDD. A pTP at 110 kDalton decreased in intensity.

Figure 8:
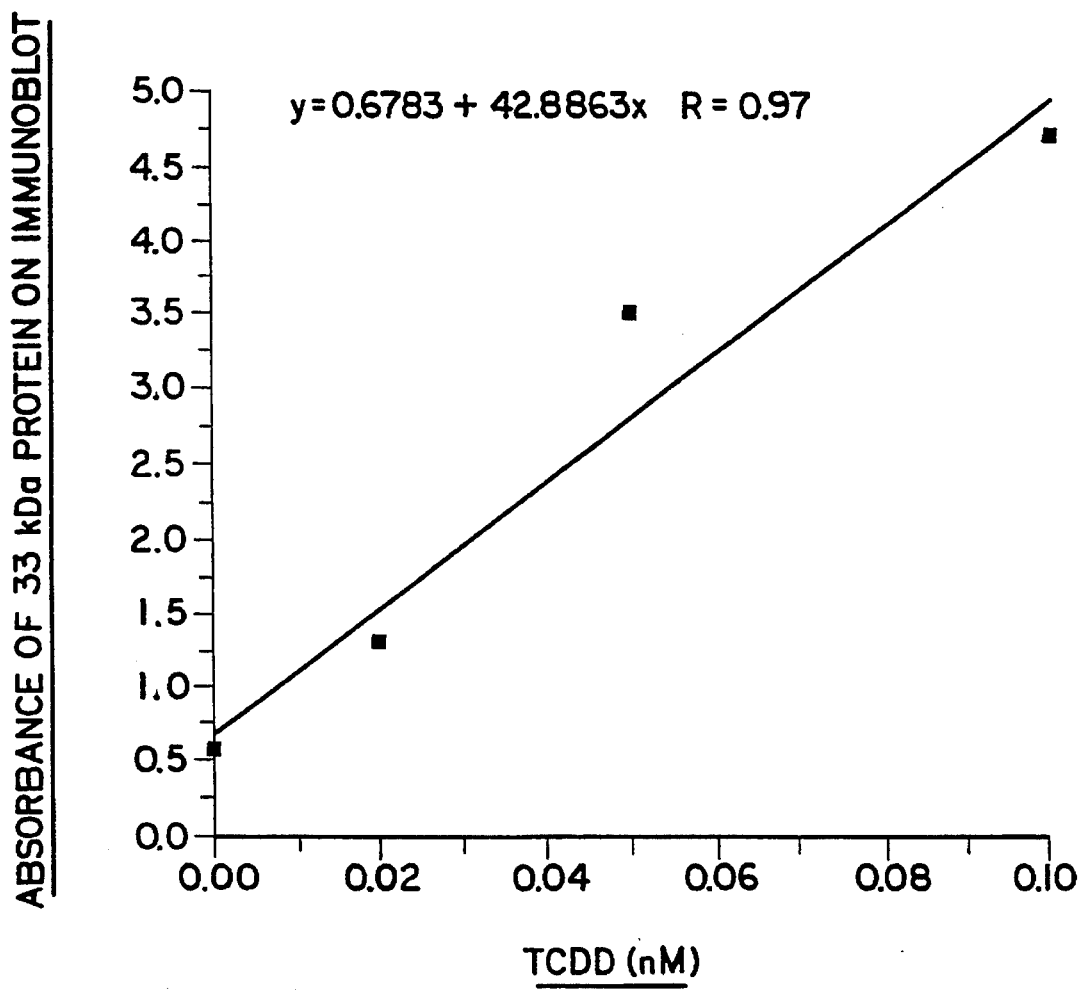
FIG. 8. Illustrates the dose-response relationship as determined by densitometer scanning of the 33 kDalton protein visualized by immunoblotting for the example in which X3 human lymphoblastoma cells were exposed to various concentrations of 2,3,7,8-tetrachlorodibenzo-p-dioxin as described in Example 2, Section entitled: Cell cultures. Immunoblots were performed with antiphosphotyrosine monoclonal antibody and the response measures protein tyrosylphosphorylation of a 33 kDalton protein 16 hours after exposure. Maximal tyrosylphosphorylation for the 33 kDalton protein was observed at 0.1 nM TCDD and the $EC_{50}$ was 0.04 nM TCDD.

FIG. 8 illustrates the dose-response relationship as determined by densitometer scanning of the 33 kDalton protein visualized by immunoblotting of total X3 cell lysate with antiphosphotyrosine monoclonal antibody. Tyrosylphosphorylation was maximal for the 33 kDalton protein at 0.1 nM TCDD and the $EC_{50}$ was 0.04 nM TCDD. This finding represents the most sensitive biological indicator of TCDD exposure reported.

Figure 9:
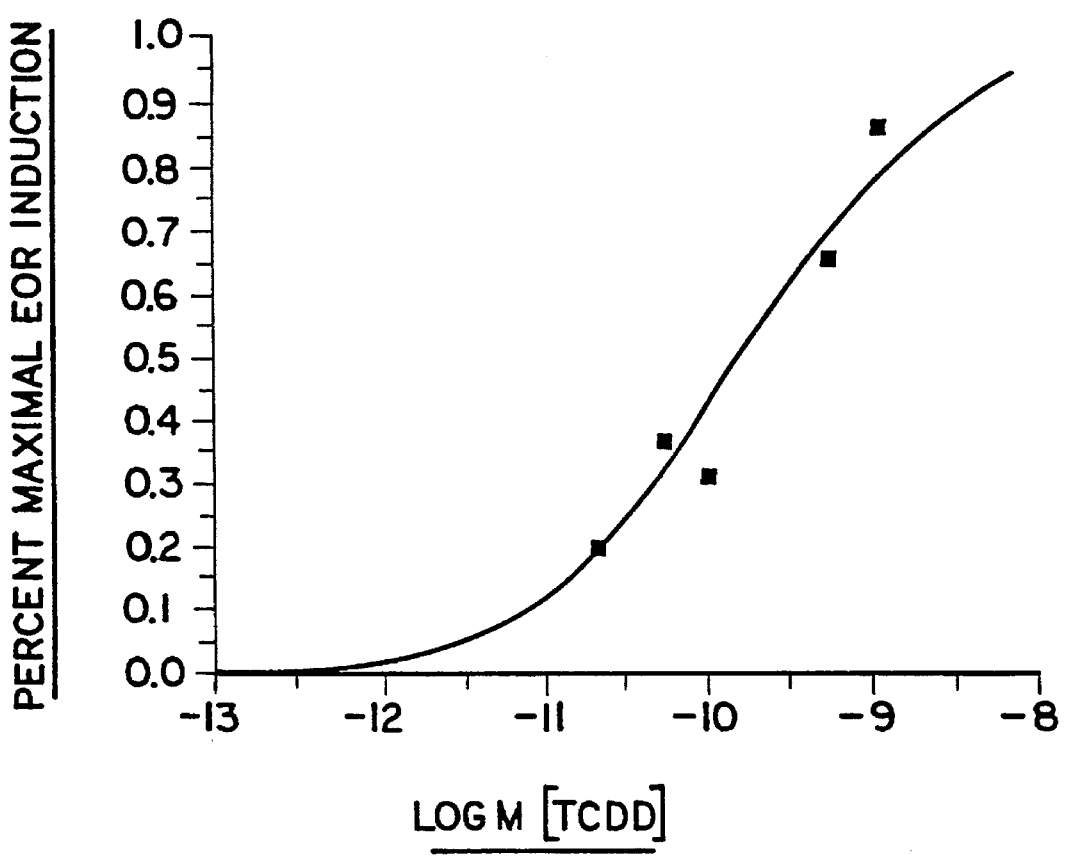
FIG. 9. Illustrates a probit modeling of the dose-response relationship as determined by ethoxyresorufin O-deethylase assay (EROD) for the example in which X3 human lymphoblastoma cells were exposed to various concentrations of 2,3,7,8-tetrachlorodibenzo-p-dioxin (TCDD) as described in Example 2, Section entitled: Cell cultures. EROD measures total cell lysate cytochrome P-450IA1 as pmol of resorufin generated per $10^9$ cells-minute 16 hours after dosing. Maximal EROD activity was observed at 1 nM TCDD and the $EC_{50}$ was 0.3 nM.

The induction of cytochrome P-450IA1 by TCDD in X3 cells is depicted in FIG. 9. Maximal EROD activity was observed at 2 nM TCDD and the $EC_{50}$ was 0.3 nM. The dose-response relationship as determined by Ethoxyresorufin O-deethylase assay (EROD) was modeled as a probit response curve with TCDD exposure.

This example supports the novel findings of Example 1, and extends them to include signal transduction effects of TCDD in a transformed cell line of human origin. As seen in vivo, exposure to TCDD resulted in an increase in intracellular protein tyrosine phosphorylation. At least 6 cellular proteins demonstrated an increase in tyrosine phosphorylation with increasing dose of TCDD. A seventh protein, a 57 kDalton protein, exists constitutively in an extremely low state of tyrosylphosphorylation in the X3 cell. In response to TCDD exposure, the 57 kDalton protein was highly phosphorylated at tyrosine residues. A single pTP at 110 kDaltons decreased with increasing TCDD concentration. As with normal cells exposed in vivo, the increased pTP observed with TCDD exposure was antecedent to the increase in cytochrome P-450IA1.

In X3 cells the increase in total pTP were observed over the same dose range of TCDD as the induction of cytochrome P-450IA1. The dose-response curves of the two effects nearly overlapped. Both effects were entirely described within 1 log unit of dosing; the $EC_{50}$s for total pTP and EROD were 0.13 and 0.3 nM, respectively. However, maximal tyrosylphosphorylation of the 33 kDalton protein was observed at 0.1 nM and the $EC_{50}$ was 0.04 nM. Specific pTP as demonstrated by the 33 kDalton protein was 10 times more sensitive an indicator of TCDD exposure than the induction of cytochrome P-450IA1.

This overlap of the 2 dose-response curves certainly implies a common mediator for overall pTP and cytochrome P-450IA1 expression. As with the in vivo pTP response, the evidence strongly indicates that the pTP response to TCDD in X3 cells is mediated by the Ah receptor.

EXAMPLE 3

Utility

A practical use for the C57BL/6 in vivo and X3 in vitro assays is to provide a method which can be employed in an economical and rapid biological assay for any substance having dioxinlike chemical activity. Illustratively, methods such as the following can be employed to identify negative samples for dioxinlike activity and separate them from samples of concern, thereby allowing subsequent high resolution chemical analysis to be reserved for relevant samples that do exhibit dioxinlike activity.

A. In vivo Determination of Dioxinlike Activity

A diethyl ether extract of a sample (3 volumes of diethyl ether: 1 volume of sample) is made by allowing the sample to be in contact with the diethyl ether for a minimum of 10 minutes in a closed container. The diethyl ether is removed to a conical tube and the solvent is evaporated to dryness at 25° C. The residue is solubilized in a minimal amount of corn oil with the application of mild heating only if necessary. The corn oil solution or suspension is administered to the C57BL/6 mice for the detection of biological activity as described in the Example 1 Sections entitled: Animals, ELISA and Immunoblots. The appearance of a densely staining 37 kDalton phosphotyrosylprotein in the immunoblot is indicative of dioxinlike activity in the sample. Quantitation of the dioxinlike activity can be performed by comparing the ELISA results with those of a standard curve or by means of a densitometer scan of any of the six phosphotyrosylproteins that increase due to the dioxinlike activity in the sample.

An estimate of the limit of detection of dioxinlike activity can be made using the 0.25 μg/kg dose as the minimally effective dose. At this level of administration of TCDD, the 37 kDalton band becomes easily visible. Assuming a 20 g mouse, the diethyl ether extract would have to contain 5 ng of dioxin equivalents to initiate a tryosylphosphorylation of the 37 kDalton protein. This amount would be present in the extract of a 10 g sample containing 400 parts per trillion of dioxin equivalents. The most relevant use of the in vivo bioassay would be for the determination of the bioavailability of dioxinlike chemicals from various environmental matrices such as air, water or soil.

B. In vitro Determination of Dioxinlike Activity

A diethyl ether extract of a sample (3 volumes of diethyl ether: 1 volume of sample) is made by allowing the sample to be in contact with the diethyl ether for a minimum of 10 minutes in a closed container. The diethyl ether is removed to a conical tube and the solvent is evaporated to dryness at 25° C. The residue is solubilized in a minimal amount of dimethylsulfoxide with the application of mild heating only if necessary. The dimethylsulfoxide solution or suspension is administered to the X3 cell culture for the detection of biological activity as described in the Example 2 Sections entitled: Cell cultures, ELISA and Immunoblots. The appearance of a densely staining 57 kDalton phosphotyrosylprotein in the immunoblot is indicative of dioxinlike activity in the sample. Quantitation of the dioxinlike activity can be performed by comparing the ELISA results with those of a standard curve or by means of a densitometer scan of any of the six phosphotyrosylproteins increase due to the dioxinlike activity in the sample.

An estimate of the limit of detection of dioxinlike activity can be made using the 0.2 nM dose as the minimally effective dose. At this level of administration the 57 kDalton band becomes easily visible. Assuming a 100 μL incubation well (e.g., in a 96 well microtiter plate), the diethyl ether extract would have to contain approximately 37.5 pg of dioxin equivalents to initiate a tyrosylphosphorylation of the 57 kDalton protein. This amount would be present in the extract of a 2 g sample containing 20 parts per trillion of dioxin equivalents. If the 33 kDalton protein were used to quantitate the dioxinlike activity, the limit of detection based upon a response at the $EC_{50}$ of 0.04 nM, would be approximately 4 ppt. Since it is generally believed that an action concentration of dioxin is 50 ppt and current instrumental methods detect approximately 3.5 ppt, this level of analysis is sufficient for initial regulatory or health considerations.

EXAMPLE 4

The X3 in vitro assay described can be employed as an economical and rapid biological assay for the assessment of human or animal exposure to dioxinlike compounds. A blood sample can be obtained from a human or animal; the lymphocytes can then be separated by well established procedures such as centrifugation on a ficoll gradient. The lymphocytes are treated as described in the Example 2 Sections entitled: ELISA and Immunoblots. The appearance of an easily visible 57 kDalton pTP would indicate exposure to dioxinlike compounds. A faint band on the immunoblot would be a negative result.

EXAMPLE 5

The X3 in vitro assay can be employed in an economical and rapid assay for the assessment of Ah receptor phenotype. Any cell type can be treated with 0.5 nM TCDD as described in the Example 2 Sections entitled: Cell culture, ELISA and Immunoblot. The appearance of an increase in pTP in the TCDD treated cells versus the untreated controls of the same cell line would indicate the presence of Ah receptor with high affinity for dioxinlike compounds. No increase in pTP would indicate the cells possessed the Ah receptor with the low affinity phenotype for TCDD. This information has potential use in the treatment of breast cancer, since it has been established that breast tumor cells with low cytochome P-450IA1 inducibility respond to chemotherapy differently than breast tumor cells with high cytochrome P-450IA1 inducibility (Thomsen, J. S., Nissen, L., Stacey, S. N., Hines, R. N., and Autrup, H.EurJ, Biochem 197, 577, 1991). Phenotyping other types of cancers, such as colon tumor cells, would also be useful clinically. The advantages inherent in the pTP determination are the shorter exposure period and the potential for finer phenotyping of the response in relation to the appearance of multiple pTP bands.

EXAMPLE 6

Lysates of X3 lymphocytes (or any cell line with inducible cytochrome P-450IA1) can be employed in a rapid biological assay for dioxinlike compounds that can be performed in a single afternoon under field conditions. An overnight culture of X3 cells is centrifuged at 2600 rpm and resuspended in PBS containing 10 nM vanidate to a density of $10^9$ cells per 100 μL and homogenized.

One-hundred μL aliquots of the homogenate are added to each well of a 96-well microtiter plate. The plates are prepared for assay by incubating overnight at 4° C. and washing with 0.05% Tween 20 in PBS. Following this preparation step, the plates may be stored at 20°–25° C. for one day. A diethyl ether extract of the test sample (3 volumes of diethyl ether: one volume of sample) is made by allowing the sample to be in contact with the diethyl ether for a minimum of ten minutes in a closed container. The diethyl ether is removed to a conical tube and the solvent is evaporated to dryness at 25° C. The residue is solubilized in a minimal amount of dimethylsulfoxide with the application of mild heating only if necessary. Add to each well 100 μL of a 2 nM ATP solution followed by 5 μL of the DMSO stabilized extract and incubate this mixture for ten to fifteen minutes at 25°–37° C. Wash all wells with 0.05% Tween 20 in PBS and saturate with 0.2 mL bovine serum albumin for five minutes at 37° C. Wells are then incubated with antiphosphotyrosine monoclonal antibody (1.5 mg per mL ascites fluid in 1 mg per mL bovine serum albumin and 0.05% Tween 20 in PBS) for five minutes at 37° C. to allow for binding. Incubation with horseradish peroxidase-linked antimouse IgG ($0.5 \times 10^{-3}$ mg IgG/mL PBS) and subsequent washing are performed immediately. Peroxidase activity is determined upon incubation with substrate (0.03% $H_2O_2$ and 1 mM 2,2'-azinodi(d-ethyl-benzthiazoline sulfonic acid) dissolved in 100 mM sodium citrate (pH 4.2) at 22° C. At the first visualization of color change, $A_{415}$ values are recorded.

Figure 10:
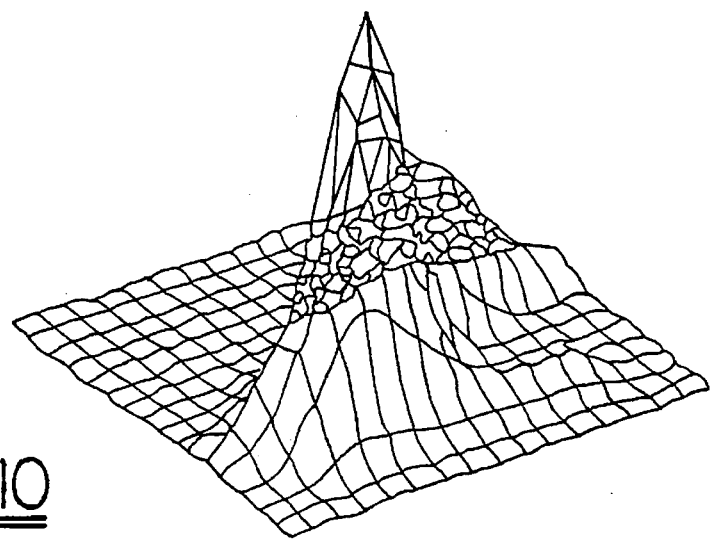
FIG. 10. A three-dimension plot of dioxin concentrations determined from a grid sampling pattern at a source point of contamination. The surface of the grid represents east-west and north-west coordinates for 272 sampling points. Vertical response represents the concentration of dioxinlike material in each of the samples.

$A_{415}$ values are determined on a microtiter plate reader—any commercial variety. A three-dimensional plot of dioxinlike compounds can be made from the $A_{415}$ values plotted on north-south/east-west coordinates. The vertical responses represent the concentration of dioxinlike material in each of the samples as shown in FIG. 10. Not counting time required for the sampling procedure, several hundred assays can be performed in a single day.

A modification of the above procedure can be used when a purified or semi-purified Ah receptor complex is used in place of the whole cell lysate. A further modification of the above procedure consists of the use of a purified or semi-purified Ah receptor complex and a protein to be phosphorylated is used in place of the whole cell lysate. Further modification of the kit microtiter assay includes the use of a purified or semi-purified Ah receptor complex in place of the whole cell lysate, and the determination of Ah receptor transformation by dioxinlike compounds by means of a monoclonal antibody to an epitope of the transformed Ah receptor, made according to techniques well known in the art. The activation (transformation) of the Ah receptor is illustrated in FIG. 11.

Figure 11:
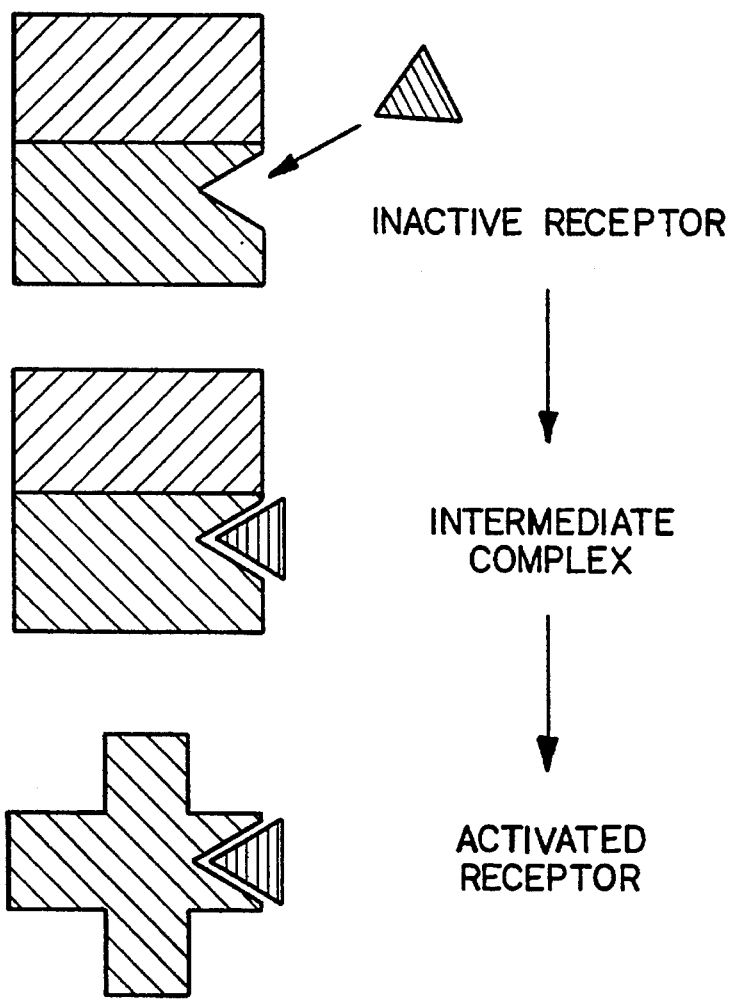
FIG. 11. A schematic representation of the Ah-receptor interacting with dioxinlike compounds. Dioxinlike compounds are represented by a dark triangle.

In the model shown in FIG. 11, Ah receptor has at least two components, though these may also exist as two domains of the same molecule. As used herein, receptor includes all molecules that interact with a ligand whether or not the receptor is found extending from the cell surface membrane and capable of binding to the ligand. Ligand is similarly defined to include any environmental or endogenous material that functions as a ligand within an organism. The interaction of the Ah receptor and a dioxinlike compound (ligand) results in a three-dimensional transformation of the complex. Since the number of transformed complexes is proportional to amount of dioxinlike compound present, antibodies to the transformed complex can be used to quantitate the concentration of dioxinlike compounds.

EXAMPLE 7

Polyclonal antibodies, which can measure the presence and amount of dioxinlike compounds have been prepared. Their preparation, characteristics, and use are desribed below.

Chemicals As in Example 1.

Antigen Synthesis and Antisera Production

Multiple antigen peptide synthesis (MAPS) was based on a portion of the $NH_2$ terminal of the Ah receptor as reported by Poland et al. (Molecular Pharmacology, vol. 39, pp. 20–26, 1990). The MAPS antigen consisted of the synthetic peptide $H_2N$-LYS-ARG-ARG-LYS-PRO-VAL-GLY-COOH referred to as SEQ ID NO:1 coupled through the carboxyl end of the peptide to a branched lysine septamer. Ratio of peptide to lysine septamer was 8:1. Purity of the antigen was 38% by weight based on amino acid analysis. The antigen was synthesized under contract by TAES laboratory, Entomology Department, Texas A&M University, College Station, Tex. 77843.

Crude antigen was dissolved in phosphate buffered saline at a concentration of 2 mg/ml and 0.5 ml aliquots were mixed with equal volumes of Freund's complete adjuvant (for first immunizations) or Freund's incomplete adjuvant (for subsequent immunizations). Immunizations consisted of 1 ml (380 μg antigen) injected subcutaneously into Flemish Giant/Chinchilla cross rabbits. Immunization schedule was as follows: Injections on day 0, 21, 35, and 49 with blood collection on day 63. Immunizations and blood collection was performed under contract by Cornell Research Animal Resources, Cornell University, Ithaca, N.Y. 14853.

Blood was clotted overnight at 10° C. and the sera isolated by two 20 minute centrifugations at 2900 RPM in an IEC centra-7 centrifuge. One ml aliquots were frozen at −80° C. until further use.

Animals

Two adult female New Zealand white rabbits (animal 321 and 377) were obtained from the NYS College of Veterinary Medicine. Rabbits were fed standard Agway rabbit pellets (Agway, Cortland, N.Y.) and received tap water ad libitum. Each animal received a single 50 mg intradermal injection of the antigen described above (hereinafter referred to as "MAPS") in Freunds complete adjuvant. Three weeks later, this procedure was repeated. Eight weeks after the first injection, 25 mL of blood was drawn from each animal. Serum was prepared from the blood, placed in 1 mL tubes, frozen and stored at −80° C. Antisera was prepared as before.

Mouse hepatic cytosol was prepared from female, C57BL/6 mice (or any cytochrome P450IA1 inducible strain). Mice were obtained from Jackson Laboratories (Bar Harbor, Me.). Experiments were performed using four to six week old, female mice weighing approximately 16 to 20 g. Mice were fed Prolab RMH 1000 rat, mouse and hamster food (Agway, Cortland, N.Y.) and received tap water ad libitum. All mice were housed three to five per cage and maintained on a photoperiod of 12 hours. Hepatic cytosol fractions were prepared by homogenizing the liver in 3 times the volume of MENG buffer (Poland et al., Molecular Pharmacology, vol. 39, 20–26, 1990). Following a 9000×g centrifugation for 20 minutes, the supernatant (S-9) was centrifuged at 100,000×g for 60 minutes and the resulting cytosol fraction was carefully removed and quickly frozen for storage at −80° C.

Immunoblots

As in Example 1.

Results

Figure 12:
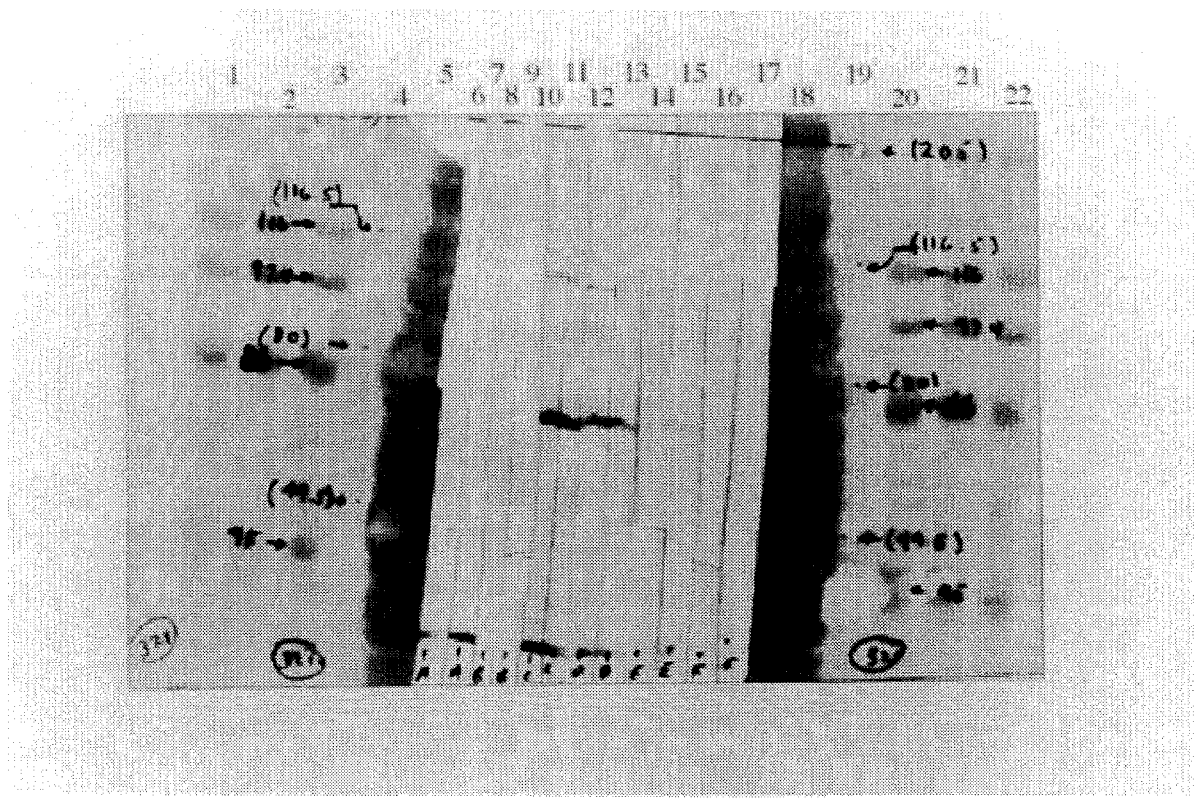
FIG. 12. Recognition of mouse liver cytosol proteins by anti-MAPS Antiserum 321. Lanes 5–11 and 13 depict antiserum recognition of 100 kDalton non-ligated form of the Ah receptor at various dilutions of antiserum.

In FIG. 12, lanes 1–3 and 20–22 represent protein standards stained for protein. Standards were (from top to bottom) 116, 97.4, 66 and 45 kDaltons. Lanes 4 and 19 were pre-stained protein standards; these were 205, 116.5, 80 and 49.5 kDaltons, top to bottom, respectively. Total cytosol stained for protein appears in lanes 5 and 18. All other lanes were immunostained with antisera.

The following antisera (with dilution) were used. Anti-MAPS 321-1 (1:11) in lanes 6 and 7, anti-heat shock Protein 90 (HSP90, Source) (1:500) in lane 8, anti-MAPS 321-2 (1:11) in lanes 10 and 11, anti-MAPS 321-2 (1:50) in lanes 12 and 13, anti-MAPS 321-2 (1:250) in lanes 14 and 15, and anti-MAPS 321-2 (1:1000) in lanes 16 and 17. The results indicate that at the second bleeding rabbit 321 was producing antibodies capable of recognizing the 100 kDalton, nontransformed state of the Ah receptor at a titer of 1:50.

Figure 13:
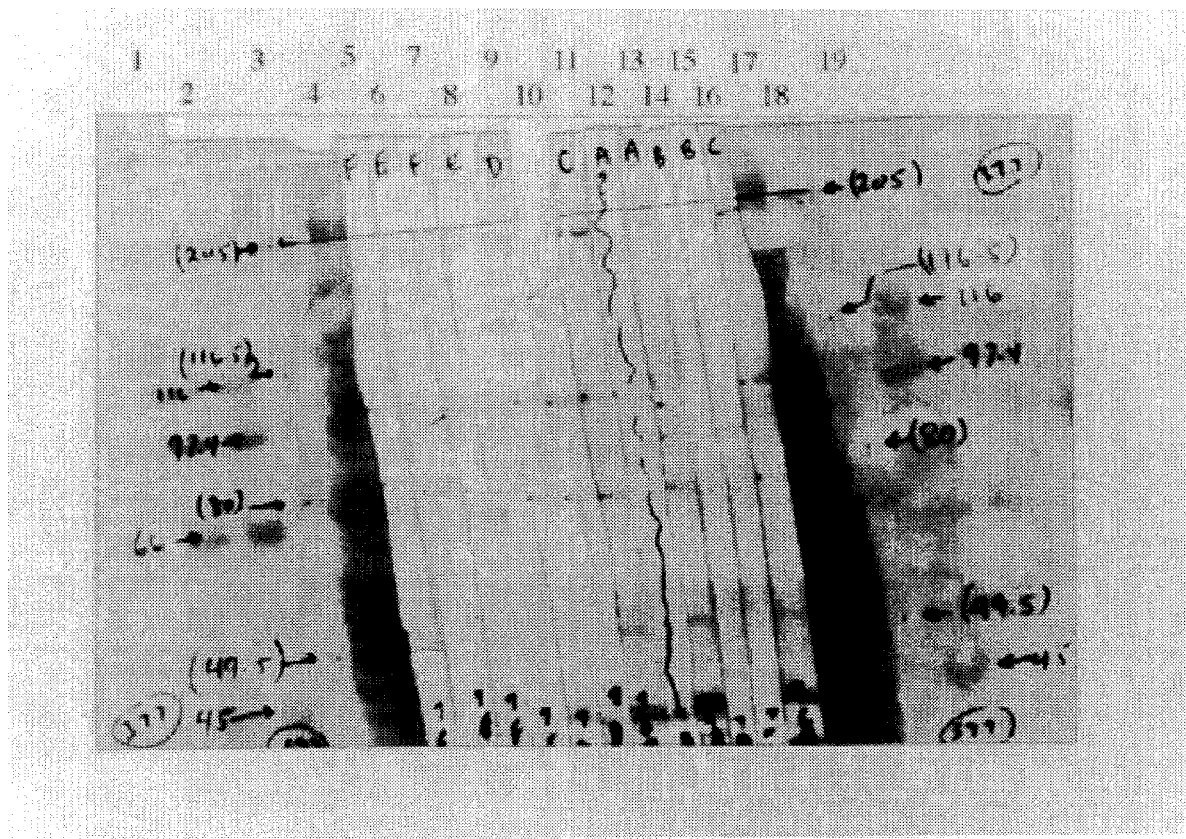
FIG. 13. Recognition of mouse liver cytosol proteins by anti-MAPS Antiserum 377. Lanes 1, 2 and 19 are protein standards stained for protein. Lanes 5 and 18 are cytosol stained for protein. Lanes 12 through 15 depict antisera recognition of 100 kDalton non-ligated form of the receptor.

Lanes 1, 2 and 19 of FIG. 13 represent protein standards stained for protein. Molecular weights represented were 116, 97.4, 66 and 45 kDaltons. The pre-stained standards in lanes 3 and 18 represent molecular weights of 205, 116.5, 80 and 49.5 kDaltons. Cytosol stained for protein was in lanes 4 and 17. All other lanes were immunostained with antisera. The following antisera (with dilution) were used: Anti-MAPS 377-2 (1:1000) in lanes 5 and 7, anti-MAPS 377-2 (1:250) in lanes 6 and 8, anti-MAPS 377-2 (1:50) in lanes 9 and 10, anti-MAPS 377-2 (1:11) in lanes 11 and 16, anti-MAPS 377-1 (1:11) in lane 13 and anti-HSP90 (1:500) in lanes 14 and 15. These results demonstrate that, at the second bleeding, rabbit 377 was producing antibodies capable of recognizing the 100 kDalton, nontransformed state of the Ah receptor at a titer of 1:250.

Antisera 321-2 and 377-2, prepared against an amino acid sequence of the N-terminus of the Ah receptor, were both capable of recognizing the Ah receptor in which it exists prior to interacting with TCDD or dioxinlike compounds. Such antisera could be used as an assay for dioxinlike compounds by quantitating the amount of nontransformed Ah receptor present in an environmental extract of air, water or soil. Quantitation could be performed by ELISA techniques, as previously described.

EXAMPLE 8

Receptor-Ligand Assays

The described procedures represent the first example of ligand quantitation by the observation of structural and/or functional changes in a receptor. The methods described herein would be suitable to assay other ligands in addition to dioxinlike compounds. Another example of this technique would be in the determination of the biologically active concentration of a peptide or 10 protein pharmaceutically based on the determination of a structural or enzymatic (functional) change in a cellular receptor or a natural or synthetic portion of a cellular receptor.

The direct and indirect immunoassays described above are based on receptor-ligand interactions and subsequent cellular signal transduction through protein tyrosyl phosphorylation. A similar bank of direct and indirect immunoassays such as those described for dioxinlike compounds can be developed for other examples of receptor-ligand interactions and other cellular signal transductions that may take place subsequent to such receptor-ligand interaction. Examples of suitable receptor-ligand interactions include carcinogen binding protein and benzo(a)pyrene, EGF receptor and epidermal growth factor agonists and antagonists, insulin receptor interactions with insulin agonists and antagonists, and estrogen receptor with estrogen agonists and antagonists.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

While the present invention has been particularly described with respect to certain preferred embodiments, various changes and modifications will be readily apparent to those of ordinary skill in the art without departing from the spirit and scope of the invention. The present invention should not be limited solely to the described embodiments. Rather, the appended claims should be interpreted to cover the aforesaid changes and modifications and equivalents.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of detecting, in a test sample, polychlorinated dibenzodioxins, polychlorinated dibenzofurans, and structural analogs thereof which exhibit biological activity of polychlorinated dibenzodioxins and polychlorinated dibenzofurans, said biological activity comprising phosphorylation of tyrosine residues of S-9 supernatant fraction proteins, said method comprising:

administering the test sample to a female C57BL/6 mouse at a dose of 2.0 µg/kg or less of the polychlorinated dibenzodioxins, polychlorinated dibenzofurans, and structural analogs thereof;

examining immunologically the mouse's hepatic S-9 supernatant fraction for phosphorylation of tyrosine residues of the S-9 supernatant fraction proteins; and correlating the phosphorylation level to the presence of polychlorinated dibenzodioxins, polychlorinated dibenzofurans, and structural analogs thereof in the test sample.

2. A method of detecting, in a test sample, polychlorinated dibenzodioxins, polychlorinated dibenzofurans, and structural analogs thereof which exhibit biological activity of polychlorinated dibenzodioxins and polychlorinated dibenzofurans, said biological activity comprising phosphorylation of tyrosine residues of S-9 supernatant fraction proteins, said method comprising:

administering the test sample to an X3 lymphoblastoma cell line at a concentration of 1.0 nm or less of the polychlorinated dibenzodioxins, polychlorinated dibenzofurans, and structural analogs thereof;

lysing cells of the cell line to form a cell lysate;

examining immunologically the cell lysate's S-9 supernatant fraction for phosphorylation of tyrosine residues of the S-9 supernatant fraction proteins; and correlating the phosphorylation level to the presence of polychlorinated dibenzodioxins, polychlorinated dibenzofurans, and structural analogs thereof in the test sample.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 7 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:1:

Lys Arg Arg Lys Pro Val Gly
1               5